(12) United States Patent
Kralick et al.

(10) Patent No.: US 8,206,334 B2
(45) Date of Patent: Jun. 26, 2012

(54) IMPLANTABLE MICRO-SYSTEM FOR TREATMENT OF HYDROCEPHALUS

(76) Inventors: Francis A. Kralick, Philadelphia, PA (US); Hongseok Noh, Fort Washington, PA (US)

( * ) Notice: Subject to any disclaimer, the term of this patent is extended or adjusted under 35 U.S.C. 154(b) by 331 days.

(21) Appl. No.: 12/755,068

(22) Filed: Apr. 6, 2010

(65) Prior Publication Data
US 2010/0256549 A1    Oct. 7, 2010

Related U.S. Application Data

(63) Continuation-in-part of application No. 11/669,665, filed on Jan. 31, 2007, now Pat. No. 7,691,077.

(60) Provisional application No. 60/763,746, filed on Jan. 31, 2006.

(30) Foreign Application Priority Data

Jan. 31, 2007    (WO) ................ PCT/US2007/061393

(51) Int. Cl.
*A61M 19/00*    (2006.01)
(52) U.S. Cl. .................. 604/9; 604/8; 604/264
(58) Field of Classification Search .................. 604/8, 9, 604/46–48, 173; 606/167
See application file for complete search history.

(56) References Cited

U.S. PATENT DOCUMENTS

| | | | |
|---|---|---|---|
| 4,432,853 A | 2/1984 | Banks | |
| 5,897,528 A | 4/1999 | Schultz | |
| 6,027,863 A | 2/2000 | Donadio, III | |
| 6,030,358 A | 2/2000 | Odland | |
| 6,107,004 A | 8/2000 | Donadio, III | |
| 6,405,079 B1 | 6/2002 | Ansarinia | |
| 6,537,232 B1 | 3/2003 | Kucharczyk et al. | |
| 6,589,198 B1 | 7/2003 | Soltanpour et al. | |

(Continued)

FOREIGN PATENT DOCUMENTS

EP    0066685 B1    11/1986

(Continued)

OTHER PUBLICATIONS

International Search Report dated Nov. 16, 2007.
Supplementary European Search Report, EP07797115, Feb. 4, 2011.

*Primary Examiner* — Leslie Deak
(74) *Attorney, Agent, or Firm* — Caesar, Rivise, Bernstein, Cohen & Pokotilow, Ltd.

(57) ABSTRACT

An implantable system for the treatment of hydrocephalus has a plurality of hollow microneedles in a fixed array. The microneedles have passages there through and are of a size to extend through dura mater with a proximal end on one side of the dura mater and a distal end communicating with the venous system in an area on a second side of the dura mater. An array of microvalves associated with a proximal end of the microneedles include segments movable by a pressure build up of cerebrospinal fluid (CSF) within the interior of the brain to provide open communication between the interior of the brain on one side of the dura mater and the venous system on the second side of the dura mater. A plurality of fluid transmitting members has distal ends communicating with the microvalves and a proximal end communicating with the ventricular space of the brain. The fluid transmitting members transmit CSF from the ventricular space through the microvalves and micro needles in fluid communication with the fluid transmitting members to prevent an excessive pressure build up of CSF within the interior of the brain.

20 Claims, 8 Drawing Sheets

U.S. PATENT DOCUMENTS

| | | |
|---|---|---|
| 6,913,589 B2 | 7/2005 | Dextradeur et al. |
| 7,037,288 B2 | 5/2006 | Rosenberg et al. |
| 7,118,548 B2 | 10/2006 | Bergesen |
| 2004/0106904 A1 | 6/2004 | Gonnelli et al. |
| 2005/0043673 A1 | 2/2005 | Lieberman |
| 2005/0096580 A1 | 5/2005 | Moskowitz et al. |
| 2005/0159697 A1 | 7/2005 | Dextradeur et al. |
| 2007/0179428 A1 | 8/2007 | Kralick et al. |

FOREIGN PATENT DOCUMENTS

| | | |
|---|---|---|
| WO | 0074763 A2 | 12/2000 |
| WO | 0166065 A2 | 9/2001 |
| WO | 2007130718 A2 | 11/2007 |

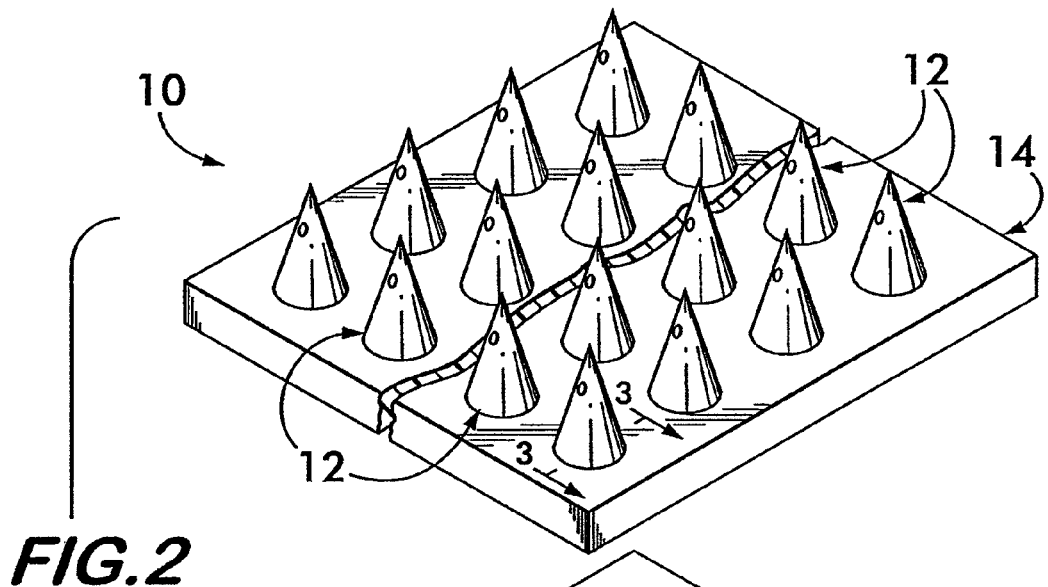
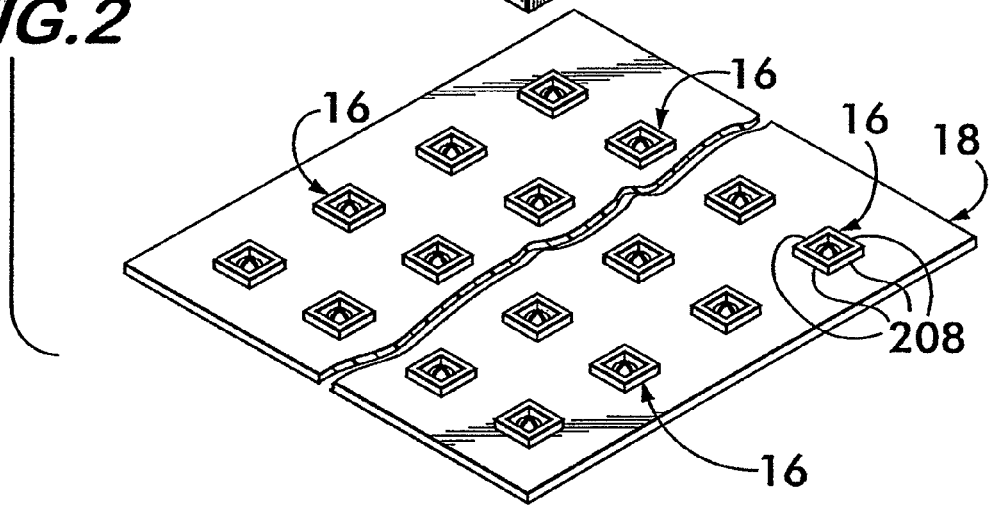
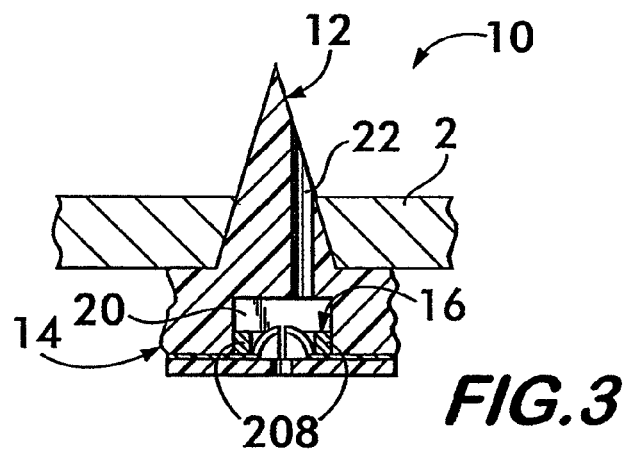

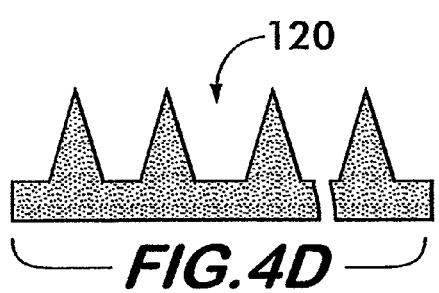
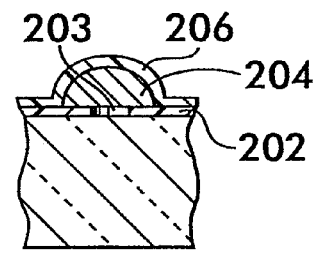
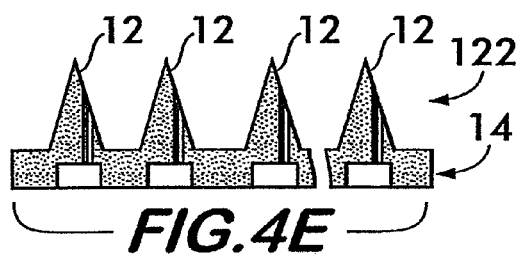
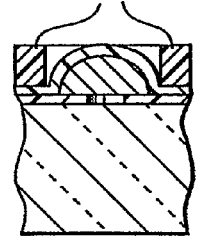
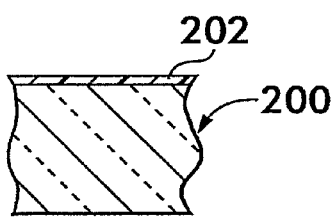
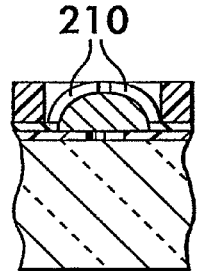
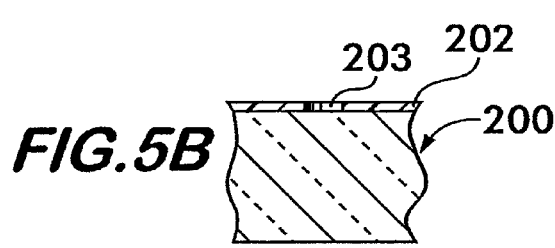
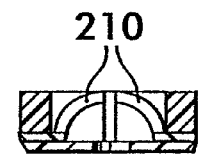
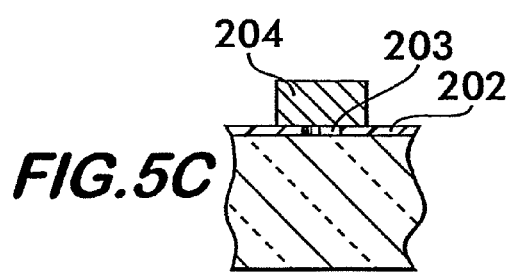
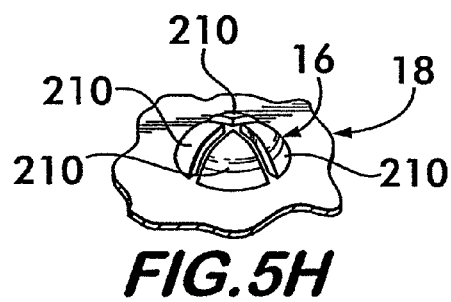

IMPLANTABLE MICRO-SYSTEM FOR TREATMENT OF HYDROCEPHALUS

RELATED APPLICATIONS

This is a continuation-in-part of U.S. application Ser. No. 11/669,665, which claims the benefit of U.S. Provisional Patent Application Ser. No. 60/763,746, filed Jan. 31, 2006, titled "Micromechanical Device for the Treatment of Hydrocephalus; Mechanical Arachnoid Villi."

BACKGROUND OF THE INVENTION

1. Field of Invention

This invention relates generally to a shunting system for treatment of hydrocephalus, and more specifically to an implantable micro-system for the treatment of hydrocephalus.

2. Description of Related Art

In order to better understand the prior art for treating hydrocephalus as well as the unique implantable micro-system of the present invention, the following brief discussion of the mechanism responsible for hydrocephalus should be helpful; although not necessary for a person skilled in the art.

Cerebrospinal fluid (CSF) is a water-like fluid produced in the brain that circulates around and protects the brain and spinal cord, as is well known to those skilled in the art. It is believed that CSF is absorbed into the superior sagittal sinus, a venous structure that drains blood from the brain, through biologic one-way valves referred to as arachnoid villi or granulations, which pierce the dura mater. The arachnoid granulations are exposed to cerebral spinal fluid that resides in the subarachnoid space on the basal side and with the venous blood of the superior sagittal sinus on the apical side. Hydrocephalus is an abnormal accumulation of CSF within the subarachnoid space of the brain due to impaired CSF absorption. As is known, the subarachnoid area is the region around the brain and is bounded by dura mater. The dura mater comprises the walls of the superior sagittal sinus.

Hydrocephalus is one of the most frequently encountered problems in neurosurgery. One of the most common methods of treating hydrocephalus is through a surgical procedure in which a tube, referred to as a "shunt," is placed into the patient's body. The shunt system for diverting CSF from the intracranial compartment was developed in the 1950's, and has remained virtually unchanged for the past 50 years.

Essentially, the prior art shunts are implanted in a human body to channel the flow of CSF away from the brain into another part of the body. These prior art shunt devices generally include a single tube provided by a proximal catheter within the ventricular space and a distal draining catheter located within an absorptive surface of the body. Between the proximal and distal ends catheters is an intervening one-way valve device that is placed subcutaneously outside of the skull to limit the flow of CSF in one direction, i.e., away from the brain and direct the flow into the absorptive surface through the distal draining catheter. The most common absorptive surface employed in the prior art is the peritoneum of the abdominal cavity. This type of shunt system is referred to as a ventriculo-peritoneal (VP) shunt. Although VP shunts have operated successfully to prevent death and disability resulting from hydrocephalus, they do have a number of shortcomings.

The first major shortcoming of the current VP shunt is its high failure rate. In fact, it has been reported in the medical literature in 1998 that approximately 40% of the VP shunts failed after one year and approximately 50% failed after two years. Moreover, it is estimated that 50% of mechanical shunt failure is due to shunt blockage, which is usually highest in the immediate post operative period. Specifically, the proximal catheter can become occluded if the brain debris or parts of choroid plexus become attached to the pores of the proximal catheter resulting in diminished flow. The valve between the proximal and distal catheters also may become occluded by debris, blood clot or infection. Bacterial infections in the blood can seed the long course of the shunt tubing from the head to the abdomen resulting in failure. Other causes of failure include tubing breakage, kinking or shortening due to patient growth or movement. All of the above-mentioned factors result in the published failure rate set forth above. As can be envisioned, this high failure rate results in frequent patient visits to the Emergency Room, frequent diagnostic procedures, hospitalizations and repeat surgery for shunt revisions. In addition to the high failure rate of prior art shunts posing a potentially dangerous situation for the patient, the high failure rate also results in increased health care costs. While the economic costs are believed to be enormous, the human cost of multiple hospital visits and surgical procedures, especially in the pediatric population simply cannot be measured.

An additional problem encountered with current VP shunts is the imprecise flow of CSF, e.g., over- or under-shunting. Under-shunting occurs when CSF is not evacuated from the brain fast enough to maintain equilibrium with its production within the brain. In this situation, the VP shunt has not adequately treated the hydrocephalus. The limitations of valve design as well as some partial occlusion can produce this under-shunting. Over-shunting is also a limitation of the current shunt design, in which too much flow is allowed through the valve to thereby create an undesired lower than normal pressure around the brain. Such a low pressure usually is exacerbated by changes in a patient's posture from a recumbent to an erect position. In addition, a siphon effect can additionally lead to problems of over-drainage.

In an attempt to solve problems of imprecise shunting programmable valves (electromagnetically adjustable) have been commercialized. One supplier of such valves is Cordis. These programmable valves permit neurosurgeons to pre-select one of multiple pressure settings of the valve at the time of implantation. After implantation, the valve can be adjusted non-invasively using a magnetic device to individualize the flow rate to a particular patient's situation. This means that surgeons are able to make adjustments to help control intracranial pressure as a function of CSF elimination. However, the actual intracranial pressure cannot be monitored after implantation. and a change in pressure setting will be variable based on whether the patient is erect or recumbent. Also, it has been reported in the literature that household magnets can change the programmable shunt valves, thereby resulting in a failure of the shunting system. Thus, the use of electromagnetically adjustable, programmable shunting valves has not proven to be a great advantage, and still being prone to other problems, such as shunt failure, breakage, clogging, and infection. Moreover, these valves do not adapt to changing patient positions once having been set.

Anti-siphon devices also have been employed to correct problems of over shunting due to changes in patient position. As reported in the medical literature, this also has not alleviated the problems associated with imprecise flow.

Recently, e.g., approximately 2004, an active shunt system was proposed, which consisted of a micro telemetry pressure sensor, a micro pump, and a controller. In this system, the controller controls the micro pump according to the intracranial pressure created by the CSF and measured with the telemetry pressure sensor. It is Applicant's understanding that pressure sensor and micro pump prototypes have been tested in-vitro. Although this particular approach could possibly provide an active form of moving CSF in relation to instantly measured pressure gradients, and also might be useful in monitoring the intracranial pressure after implantation for diagnostic purposes, there are still many obstacles to overcome with this later proposed system, e.g., power supply, complex circuitry, multiple moving parts, as well as the earlier mentioned problems of the current systems; namely, breakage, clogging, infection and the use of only a single outlet.

The following patents disclose prior art systems for the treatment of hydrocephalus:

| | |
|---|---|
| U.S. Pat. No. 4,432,853 | Banks |
| U.S. Pat. No. 5,897,528 | Schultz |
| U.S. Pat. No. 6,027,863 | Donadio, III |
| U.S. Pat. No. 6,030,358 | Odland |
| U.S. Pat. No. 6,107,004 | Donadio, III |
| U.S. Pat. No. 6,589,198 | Soltanpour et al. |
| U.S. Pat. No. 6,913,589 | Dextradeur |
| U.S. Pat. No. 7,037,288 | Rosenberg et al |
| U.S. Pat. No. 7,118,548 | Børgesen |

The present invention is believed to have the capability of overcoming virtually all of the problems associated with the prior art shunting systems, as described above.

SUMMARY OF THE INVENTION

An implantable system for the treatment of hydrocephalus has a plurality of hollow microneedles in a fixed array. The microneedles have passages there through and are of a size to extend through dura mater with a proximal end on one side of the dura mater and a distal end communicating with the venous system in an area on a second side of the dura mater. An array of microvalves associated with a proximal end of the microneedles include segments movable by a pressure build up of cerebrospinal fluid (CSF) within the interior of the brain to provide open communication between the interior of the brain on said one side of the dura mater and the venous system on the second side of the dura mater. Fluid transmitting members have distal ends communicating with the microvalves and proximal ends communicating with the ventricular space of the brain. The fluid transmitting members transmit CSF from the ventricular space through the microvalves and micro needles in fluid communication with said fluid transmitting members to prevent an excessive pressure build up of CSF within the interior of the brain.

Preferably the fluid transmitting members are micro-conduits or micro-fibers that communicate with at least 50% of the microvalves; more preferably over 50% of the microvalves and most preferably with all of the microvalves.

In the preferred form of this invention, the microvalves permit the flow of CSF through the microneedles based on the pressure differential between the ventricular space at the proximal end of the fluid transmitting members and the sinus at the distal end of said needles. The microvalves of this invention are simplistic in design, having a minimum of moving parts without the need for a power source. The microvalves employed in this invention act as many micro-sized "flap valves" that open and close in response to the pressure differential between the subarachnoid space and the venous system of the sinus thereby mimicking the function of normal arachnoid granulations.

Most preferably, the plurality of microneedles is formed in a fixed array on a first substrate and the microvalves are formed in substantially the same fixed array on a second substrate. In accordance with this embodiment, the first and second substrates are secured together, e.g., by friction fitting the valves to corresponding needles and/or by thermal bonding contiguous surfaces of the first and second substrates together.

In the most preferred embodiment of this invention, the microneedles are substantially cone shaped, including a pointed distal end adapted to penetrate through the dura mater during the procedure of inserting the microsystem in a patient's head.

Reference throughout this application to a "microneedle" means a needle having dimensions most commonly defined in micrometers, although the entire array of microneedles, as a unit, may have dimensions most commonly defined in units larger than micrometers, e.g., millimeters. Needles having dimensions outside the range of micrometers but that are capable of being maintained in an array for insertion into the skull of a human to treat hydrocephalus are considered to be within the scope of this invention. However, hollow microneedles are considered to be the most preferred needle structures for use in the systems of this invention.

Reference to "microvalve(s)" in accordance with this invention, refers to valves designed to enclose a lower, or proximal end of the passage through each microneedle and being adapted to be in an opened condition to permit the flow of CSF through the needle, when desired to preclude an excessive build up of pressure within the subarachnoid area. The number, density and location of the system of this invention may vary based on laboratory measurements, but a starting point will be an arrangement that produces a desired flow, which presently is believed to be on the order of roughly 4.52+/−0.43 microL/min per mm Hg/cm(2). That is, a plurality of individual units can be positioned in different locations within the skull and the size of the individual units can be varied to either increase or decrease the number and/or density of the microneedles in each unit.

Reference to "micro-conduits," micro-fibers," and the like mean conduits or fibers having dimensions most commonly defined in micrometers, although an entire array of micro-conduits and/or microfibers, as a unit, may have dimensions most commonly defined in units larger than micrometers, e.g., millimeters.

BRIEF DESCRIPTION OF THE DRAWINGS

The invention will be described in conjunction with the following drawings in which like reference numerals designate like elements and wherein:

FIG. 2 is a schematic, exploded, isometric view of an implantable micro-system for the treatment of hydrocephalus in accordance with this invention;

FIG. 3 is a schematic sectional view through a single microneedle of the system illustrated in FIG. 2, with the microneedle and associated microvalve assembled together and with the needle passing through dura mater in a patient's skull;

FIGS. 4A through 4E illustrate sequential steps in the fabrication of microneedles employed in the system of this invention;

FIGS. 5A through 5G illustrate sequential steps in the fabrication of the preferred dome-shaped microvalves employed in this invention;

FIG. 5H is an isometric view showing the configuration of the dome-shaped petal valve construction after the laser machining step of the valve forming process;

DETAILED DESCRIPTION OF THE INVENTION

The invention will be illustrated in more detail with reference to the following Examples, but it should be understood that the present invention is not deemed to be limited thereto.

CSF is produced in the brain (choroid plexus and ependymal lining of the ventricular space) at a rate of approximately 0.3-0.5 ml/minute. The average volume of intracranial CSF is 125 ml. The total volume of CSF is turned over 3-4 times in a 24 hour period [Pediatric Neurosurgery at the Univ. of Adelaide]. The production and absorption of CSF is therefore in a dynamic equilibrium. Although there is some controversy as to the exact mechanism by which CSF absorption takes place to thereby maintain a desired pressure level within the subarachnoid area, it is most widely held that the primary route for maintaining equilibrium is the result of CSF being permitted to move into the sinus through arachnoid granulations that pierce the dura mater of the sinus.

Specifically, the CSF pressure in the subarachnoid area varies according to age. In infants, it is estimated that the CSF pressure is between about 40 to 50 mmH$_2$O and in children, from 40-100 mmH$_2$O. In older age groups, the pressure remains constant at about 150 mmH$_2$O. Pressures above 200 mmH$_2$O are considered to be abnormal.

It also should be noted that the CSF pressure is usually about 40 to 50 mmH$_2$O above the intracranial venous pressure. This difference in pressure is related to the continuous production of CSF and the resistance to its secretion.

Hydrocephalus is described as either non-communicating or communicating. The communicating form is a defect at the level of the arachnoid granulations/villi. The non-communicating type is caused by an obstruction to outflow within the interior of the brain. These pathological conditions of hydrocephalus can be life-threatening and result in brain injury if left untreated. They are caused by a number of different etiologies and effect both the pediatric and adult patient population.

Figure 1:
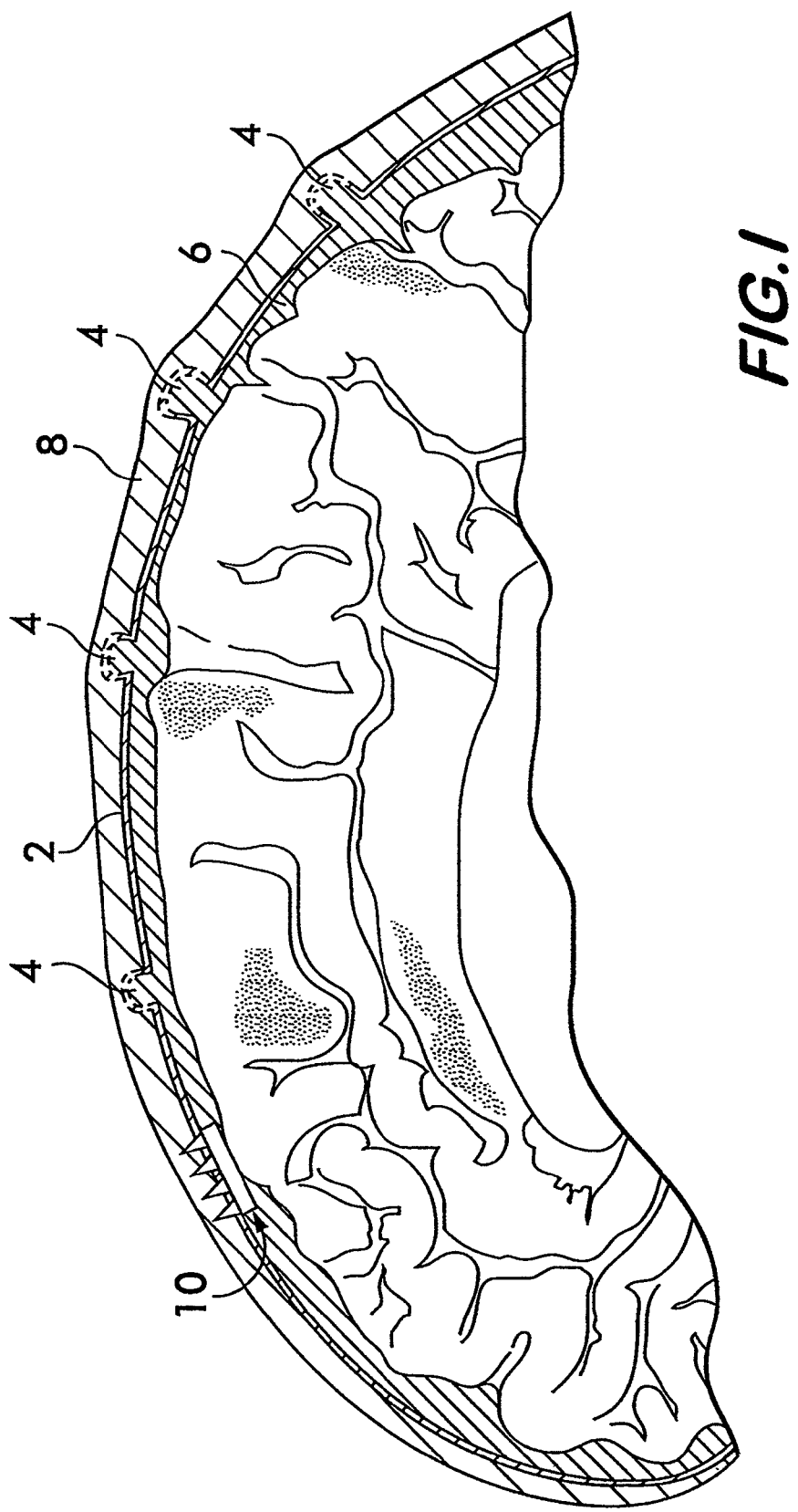
FIG. 1 is a schematic view of a skull showing a preferred location of an implanted micro-system for the treatment of hydrocephalus in accordance with this invention.

The implantable micro-system of the present invention is generally shown at 10 in FIG. 1, being implanted in the walls of the sinus that are comprised of dura mater 2. The sinus can be, but is not limited to the superior sagittal sinus. The system 10 is designed to simulate the generally normal performance of the arachnoid villi 4 in healthy patients. That is, the system 10 is designed to function as a one-way valve system to maintain a desired pressure level (or prevent an excessively high pressure level) within the brain. Specifically, the system 10 of this invention communicates the subarachnoid space 6 within the surrounding dura mater 2 with the sinus 8 (FIG. 1). To the best of Applicant's knowledge this approach in dealing with hydrocephalus has not been employed in the past and is not disclosed in any prior art.

Referring specifically to FIG. 2, the implantable microsystem 10 is schematically illustrated as including a plurality of microneedles 12 formed in a fixed array on a carrier substrate 14. The system further includes a plurality of microvalves 16 formed in a fixed array on a substrate 18, with the valves 16 disposed in substantially the same array as the microneedles 12 formed in substrate 14 so that each of the valves in the array will cooperate with a corresponding hollow microneedle.

Referring to FIG. 3, the arrangement of a single, hollow microneedle 12 and corresponding microvalve 16 is illustrated, after the assembled system 10 has been inserted through the dura mater 2 in a patient. All the needles 12 included on the substrate 14 are inserted through the dura mater in the same manner as the single microneedle 12 and corresponding microvalve 16 shown in FIG. 3. Therefore the arrangement/location of the microvalve 12 and its cooperating microvalve 16 depicted in FIG. 3 and discussed in detail hereinafter applies to all of the microvalves 12 and their cooperating microvalves in the system 10 of this invention.

Referring to FIG. 3, in a preferred embodiment of this invention each microneedle 12 is a generally cone-shaped, hollow member and extends through the dura mater that forms the walls of the superior sagittal sinus 2. An enlarged opening 20 extends through the substrate 14 and communicates with a proximal end of passage 22 extending through microneedle 12. A one-way microvalve 16 is received within the opening 20. It should be noted that a similar microvalve 16 communicates with each of the microneedles 12 in the array in the same manner as described above in connection with FIG. 3. Thus the passage(s) 22 through the needle(s) communicate with the intracranial region of the skull surrounding the brain, where CSF flows, and also with the sinus, e.g., the superior sagittal sinus. If desired a detent-like surface or recess can be formed about the conical surface at the base thereof adjacent the substrate 14 to provide a region in which the tissue of the dura mater can lock into place and thereby aid in holding the system 10 in proper position.

From the above explanation it should be apparent that Applicant has invented a unique implantable microsystem 10 that diverts CSF from the subarachnoid space 6 to the sinus 8, thereby mimicking normally functioning arachnoid granulations/villi for the treatment of hydrocephalus. The system 10 of this invention is intended to replace deficient arachnoid villi and thereby produce the physiological condition of eliminating excess CSF pressure in the brain.

As explained above, the system 10 of this invention consists of an array of microneedles 12 and microvalves 16 retained on respective substrates 14 and 18. The array of microneedles 12 is surgically placed to pierce the dura mater 2 (FIGS. 1 and 3), and, in conjunction with their corresponding one-way valves 16, act as a one-way outlet for CSF. Specifically, microvalves 16 attached at the bottom, or proximal end of the microneedles 12 are intended to divert CSF to the venous system at a given pressure. The outflow of CSF is controlled passively by the pressure differential between the venous channel and the subarachnoid space 6, in a manner very similar to a normally functioning arachnoid villi biological system. Thus, the system of this invention is intended to mimic the function of the normal CSF physiologic mechanism.

It is anticipated that the system 10 of this invention can employ as many as 100 microneedles 12 and microvalves 16 in an array on respective, substantially square substrates 14. 18, each of which is approximately 1 mm thick and has sides approximately 5 mm in length. Thus, in an embodiment wherein the microneedles 12 are disposed in a 10×10 array on a substrate having 5 mm sides, the microneedles preferably have a maximum outside dimension of less than 0.5 mm. It also is envisioned that more than one system 10 can be implanted through the dura mater, depending on the flow of CSF required to maintain a desired pressure within the subarachnoid space 6.

As explained above, the microvalves 16 and microneedles 12 are formed separately, and are included on respective substrates 14 and 18, which are joined together (e.g., by thermal bonding contiguous surfaces of the substrates together and/or by friction fitting the valves 16 within the enlarged openings 20 at the proximal end of respective needles 12—FIG. 3).

The material forming the microvalves 12 must have low rigidity (that is, have low cracking pressure), as well as being biocompatible with the body. To meet these requirements, Parylen C (poly-monochloro paraxylylene) has been selected as the material for the device. Parylene C is a biocompatible, thin polymer film that is micromachinable. Moreover, it, as well as the other materials employed in the system are compatible with current imaging modalities, such as CAT scan and MRI of the brain.

Although applicants have selected Parylene C as a preferred material for coating the needles 12 and manufacturing the valves 16, it should be understood that the specific materials employed are not considered to be a limitation on the broadest aspects of the present invention. People skilled in the art clearly will be able to select appropriate polymers and possibly other materials for use in fabricating the microneedles 12 and microvalves 16. In fact, useable materials are disclosed in an article entitled "Three dimensional MEMS microfluidic perfusion system for thick brain slice cultures," authored by Yoonsu Choi et al. and appearing in Biomed Microdevices (2007) 9:7-13. The subject matter of this latter article is hereby fully incorporated by reference herein.

It also should be understood that the specific construction of the microvalves 16 do not constitute a limitation on the broadest aspect of this invention. However, it should be noted that there are two types of valves with regard to their initial state; namely, the normally opened valve and the normally closed valve. The normally opened valves stay open until the pressure reaches a certain point at which the membrane collapses and covers the orifice (i.e., closes the valve). The normally closed valves remain closed until the pressure difference reaches a cracking pressure at which the membrane is lifted, opening the valve to provide a fluid path. In order to avoid any back flow (from sinus to the intracranial area), the normally closed valve is preferred for use in the present invention.

A number of preliminary valve designs were tested, with the two most desirable designs being selected on the basis of the ease of manufacturing and required valve parameters, e.g., cracking pressure and reverse flow prevention. The primary and most preferred design is the dome petal (DP) design, which is illustrated in FIG. 3, and will be discussed in greater detail hereinafter, with regard to its method of manufacture. The second design is the four arm corrugated spring design (not shown), which is known in the art and does not need any further explanation herein.

The dome petal design is, as the name implies, a dome with a square base and the dome being cut in four equal segments, which normally are in a collapsed, or closed condition. The four arm corrugated spring design includes four arms fixed to four positions on the surface of a base and the four arms are attached to a square shaped plug stopper. The stopper is covering a flow hole, which is cut through the base. This arrangement acts like a flexible membrane that can open and close altering the flow of the CSF from the subarachnoid space into the sagittal sinus space. As noted above, Parylene C was chosen as the valve material for both designs.

In a representative embodiment, the base of each of the valves was essentially square, having sides of approximately 300 micrometers in length and a depth or thickness of approximately 20 micrometers. An opening through the center of the base was approximately 50 micrometers in diameter. When constructed from Parylene C the base membranes had a negligible displacement of several nano-meters for a pressure difference of 100 Pa to 1000 Pa.

Both the dome petal and four arm corrugated spring designs were subjected to pressure-deflection analyses which revealed the following four points about the effects of various parameters, as follows:

1. As pressure increased across the valve, the displacement of the membrane increased.
2. As the membrane thickness increased, the displacement of the membrane decreased.
3. For the dome-petal construction, as the height of the dome increased the displacement of the membrane increased.
4. For the four arms corrugated spring construction, as the number of corrugation increases, the displacement in the membrane increased.

The four parameters associated with the performance of a check valve are cracking pressure, flow resistance in the forward direction, leakage in the reverse direction and maximum reverse blocking pressure. In order to investigate the four parameters, fluidic analysis is required to be coupled with structural analysis. People skilled in the art, clearly can investigate the operability of various different microvalves for the purpose of selecting an appropriate valve for use in the present invention.

The shunts of this invention permit the rate of CSF absorption to be tailored to the needs of the patient. By achieving this result, the invention essentially restore the normal CSF equilibrium in the face of non-functioning native absorption sites while production remains constant.

The shunt of this invention allows the efflux of CSF from the subarachnoid space as a result of the pressure differential between that area and the sinus of the vascular outflow pathways of the brain, thus giving precise control of the intracranial pressure, closely mimicking the properly functioning arachnoid villi. The present device needs to be capable of diverting the CSF at low pressure differences (<50 mmH$_2$O). Moreover, the device desirably should open for the CSF to flow out but reliably close to prevent backflow. In addition the device needs to be designed to hold the CSF in the brain at a rate of change in pressure of 150~200 mmH$_2$O.

In order to mimic the functioning of the biological arachnoid villi, the system 10 must be properly designed. Indeed, the size of the system is a critical aspect of the invention. Specifically, the size is dictated by the fact that system 10 will be surgically implanted adjacent to the brain in the subarachnoid space 6, as illustrated in FIG. 1. In particular, the system 10 will be implanted into the dura mater 2 in close proximity to the cerebral structures. Therefore, it is important that the system be small and that it have a low profile. The passive system of this invention obviates the need for multiple moving parts or for the use of any power supply. Employing active components that require a power supply and control units will make it very difficult to build a system that is sufficiently small to be placed within the confines of the skull, and also could have an adverse effect on the reliability of the system.

Moreover, the present invention has redundancy built into the system; in view of the fact that the system includes multiple needles 12 communicating the subarachnoid area with the sinus. In particular, the dura mater in a normally functional individual has many arachnoid granulations/villi to drain CSF. The system of this invention, employing multiple microneedles 12 has the same or similar redundancy. Thus, a redundant system of the type employed in the microsystem 10 of this invention should lower the failure rate relative to prior art systems that rely on a single conduit.

Another important aspect of this invention is the biocompatibility of the material with the body. Biocompatibility insures that the materials employed in the system 10 will be inert to the body and, therefore, that the body will not reject the system. In addition, blood clotting on the system also needs to be avoided to reduce the failure rate.

In summary, the micro-system 10 of this invention desirably mimics the number as well as the size of the native arachnoid villi, instead of employing a single outflow pathway to shunt CFS to a non-physiologic location as in the prior art shunting systems. Thus, the present invention provides redundancy to avoid failure as a result of clogging of a single orifice. This array of multiple outlets provided through the microneedles 12 increases the reliability of the system 10 as compared to prior art systems having only a single pathway for the flow of CSF out of the subarachnoid space.

The system 10 of this device is compact and has a high density of outflow pathways. It should be noted that maintaining the passages in close proximity could result in small obstructions potentially occluding many of the pathways. It is envisioned that this potential can be overcome by increasing the area of the system 10, while decreasing the density of the array of microneedles 12 and microvalves 16 associated with such needles. The thin profile of the system 10 will still fit against the sinus in the subarachnoid space and would more closely mimic the physiologic system in which the native arachnoid villi are located along the length of the sinus.

Many of the current shunt systems fail as a result of occlusion by the choroid plexus. The system 10 of this invention does not reside in the ventricular system but rather in the subarachnoid space that communicates with the ventricular space containing CSF because of its small size. This mode of failure is therefore eliminated. A further refinement, in accordance with alternative embodiments 300 and 400 of this invention, will be discussed in detail hereinafter with respect to FIGS. 6 through 7A and FIGS. 8, 9, respectively. These alternative embodiments 300 and 400 employ a plurality of fluid transmitting conduits or fibers e.g., micro-conduits or wicking fibers that reside within the ventricular system and communicate with the microvalves and microneedles, which allows the system to be applied to non-communication as well as communicating hydrocephalus.

A concern of obstruction inherent in the system 10 of this invention is the possible obstruction of the tips of the microneedles 12 from clotting blood. This problem is believed to be correctable by the proper selection of size and orientation of the orifices of the microneedles and also by the possible use of surface coatings on the needles to prevent clotting.

Shunt failure of prior art devices as the result of infection should also be drastically reduced with the system 10 of this invention, except possibly in cases of meningitis. Meningitis is an infection of the covering of the brain and results in the obstruction of normal arachnoid villi. Given the resemblance of the system 10 of this invention to the native arachnoid villi this could be an uncommon source of obstruction in the present invention. However, other types of infection and therefore shunt failure commonly seen with prior art shunts should be eliminated by the design of the system 10.

Moreover, shunt failure as the result of tubing disconnection, cracking, kinking and shortening as a result of patient growth is similarly eliminated by the system 10 of this invention, since the present invention does not employ any long tube connecting the subarachnoid space to the peritoneal cavity as in prior art constructions.

The system 10 in accordance with this invention is compact and completely contained within the confines of the skull. The potential for damage is minimal as it is afforded the protection of the skull. The potential for dislodgement is minimized by proper placement and anchoring.

For safety considerations, the anterior one third of the sinus would be the most logical site for implantation, as illustrated in FIG. 1. In the event of tearing the wall of the sinus during implantation this section of vasculature can be sacrificed without producing neurological deficit.

Figure 6:
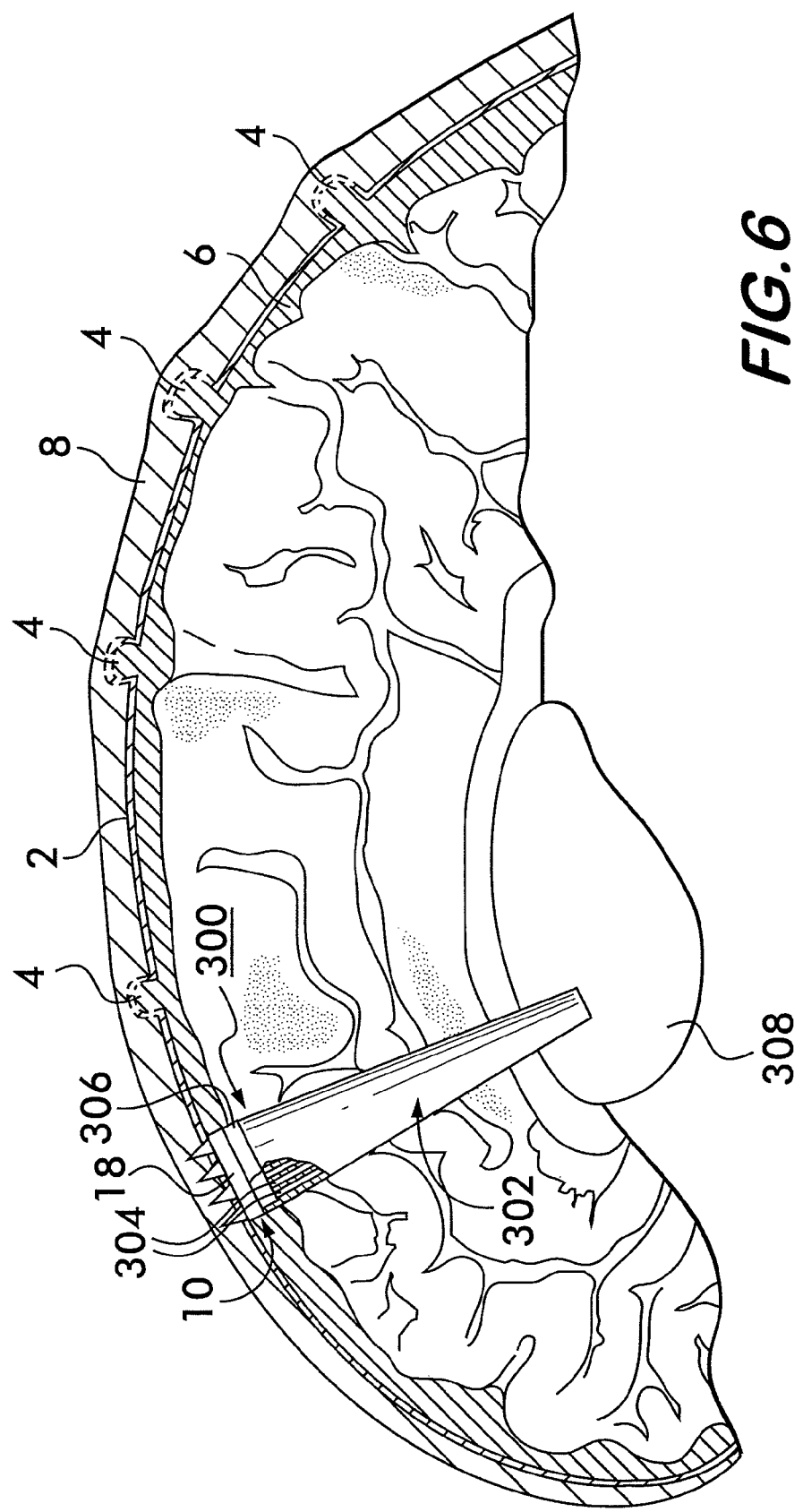
FIG. 6 is a schematic view of a skull, as viewed from the side of the head, showing a first alternative embodiment of this invention in which the implanted micro-system communicates with the ventricular space of the skull through a plurality of micro-conduits formed in a unitary member.
Figure 7:
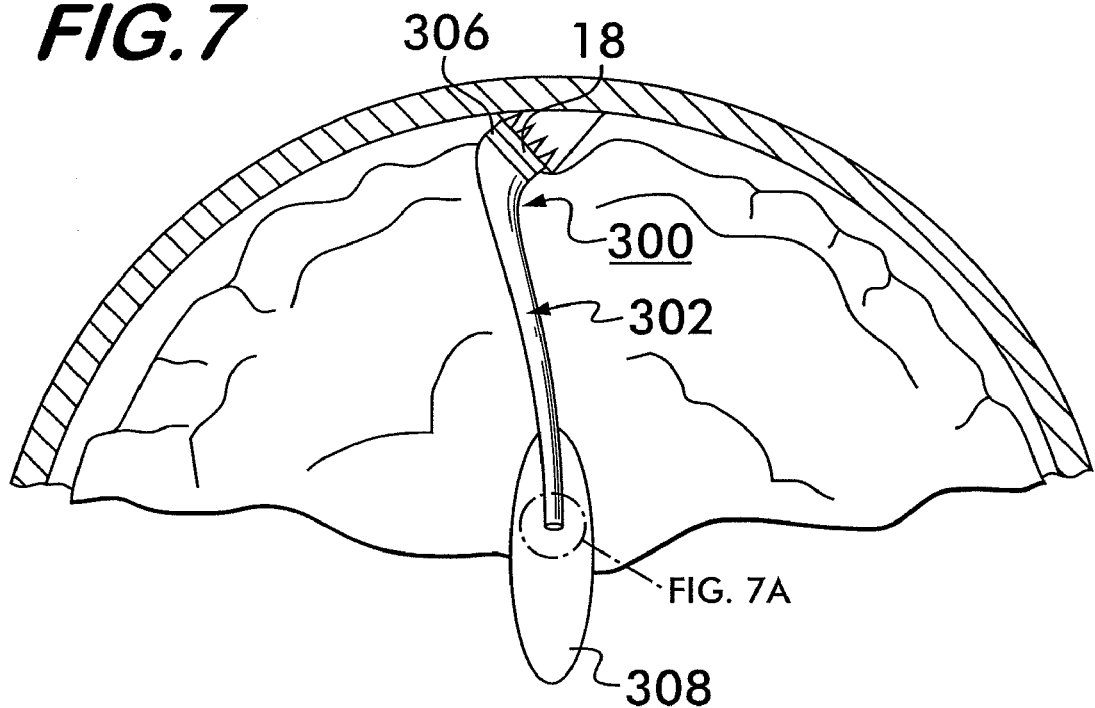
FIG. 7 is a schematic view of a portion of the first alternative embodiment, as viewed from the front of the head.
Figure 7A:
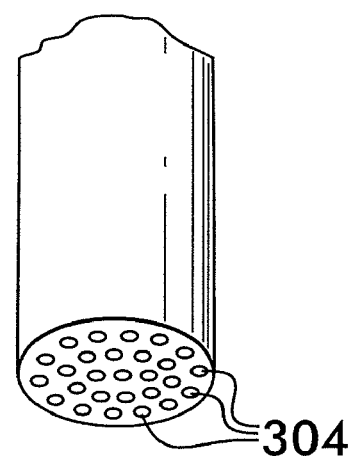
FIG. 7A is an enlarged view of the circled section identified as "FIG. 7A" in FIG. 6 showing details of the micro-conduits formed in the unitary member.

Referring to FIGS. 6, 7 and 7A, the above-identified first alternative embodiment 300 of this invention includes a fluid transmitting member 302 having a plurality of fluid transmitting micro-conduits 304 (FIGS. 6 and 7A) formed unitarily (e.g., by molding) with a plenum compartment 306 and communicating with the ventricular space 308. As illustrated, the fluid transmitting member 302 is shown in communication with the third ventricle. However, it is within the scope of this invention to also, or alternatively communicate the fluid transmitting member 302 with the lateral ventricles. By way of example, and not a limitation on the broadest aspects of this invention, the fluid transmitting member 302 can have a length of approximately 5 centimeters and a diameter of about 100 microns with the individual micro-conduits 304 having a diameter of approximately 3 millimeters As can be seen in FIGS. 6 and 7, the plenum compartment 306, in the preferred embodiment of this invention, is coterminous with the substrate 18 and therefore all of the fluid transmitting micro-conduits 304 in the member 302 communicate with all of the microvalves included in the substrate 18. However, it is within the scope of this alternative embodiment 300 to form the plenum compartment 306 of a dimension that does not communicate with all of the microvalves on the substrate 18. However, in the preferred embodiments of this invention the plenum compartment 306 should communicate with at least 50% and most preferably over 50% of the microvalves on the substrate 18. The plenum compartment 306 can be secured to the bottom surface of substrate 18 by any suitable means, such as an adhesive component that is biocompatible with the patient's body. The particular manner of securing, or fastening the plenum compartment 306 to the substrate 18 does not constitute a limitation on the broadest aspects of this invention.

It also should be apparent that the fluid transmitting member 302, including the plenum chamber 306 needs to be formed of biocompatible materials in the same manner as the other components of this invention. This issue of material selection has been discussed in detail earlier in this application and will not be repeated herein for purposes of brevity. Suffice it to state that individuals skilled in the art clearly will be able to select suitable materials for use in the embodiment of this invention illustrated in FIGS. 6, 7 and 7A, and the specific materials employed do not constitute a limitation on the broadest aspects of this invention.

Figure 8:
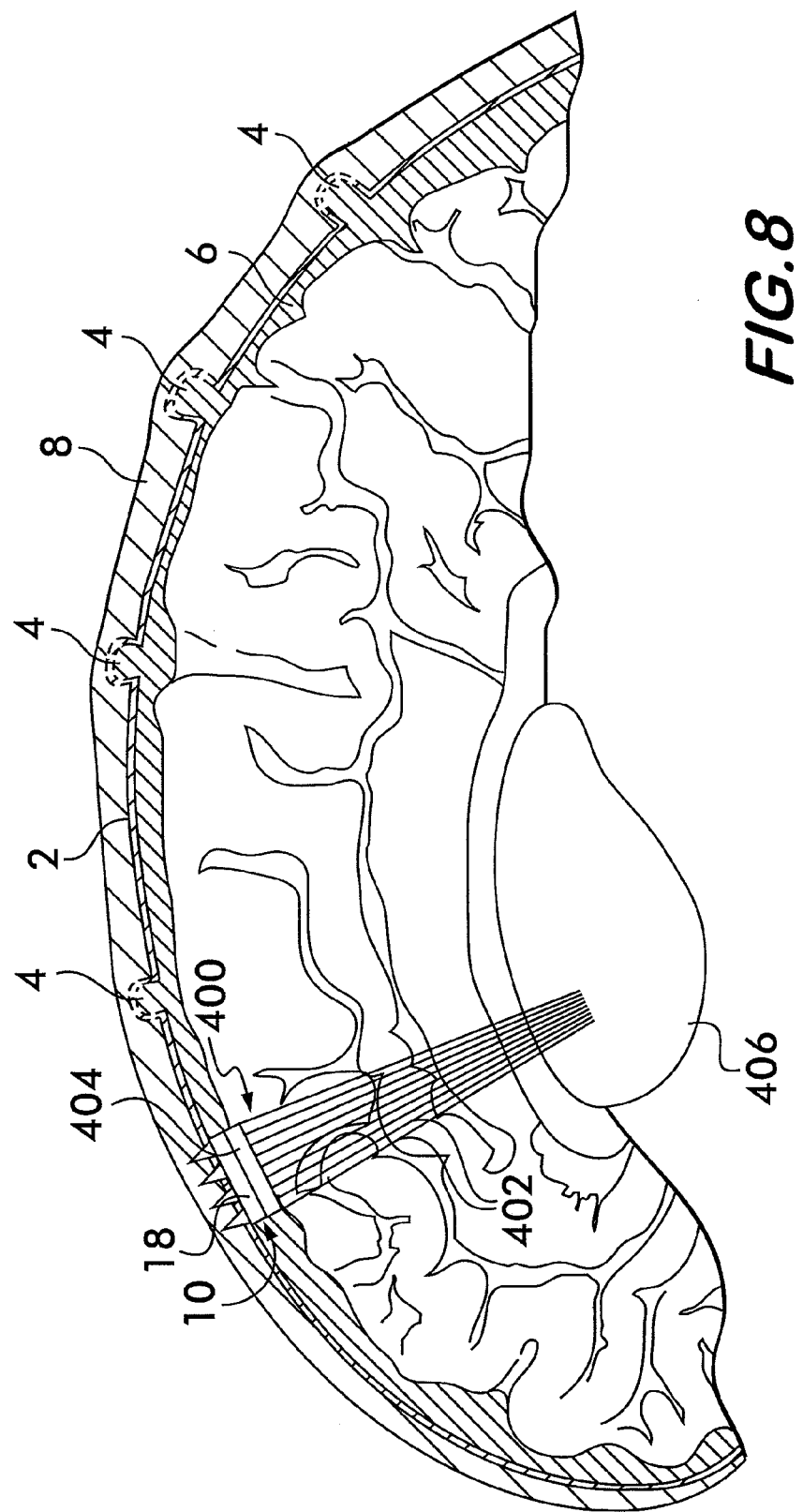
FIG. 8 is a schematic view of a skull, as viewed from the side of the head, showing a second alternative embodiment of this invention in which the implantable micro-system communicates with the ventricular space of the skull through a plurality of individual micro-conduits or fibers.
Figure 9:
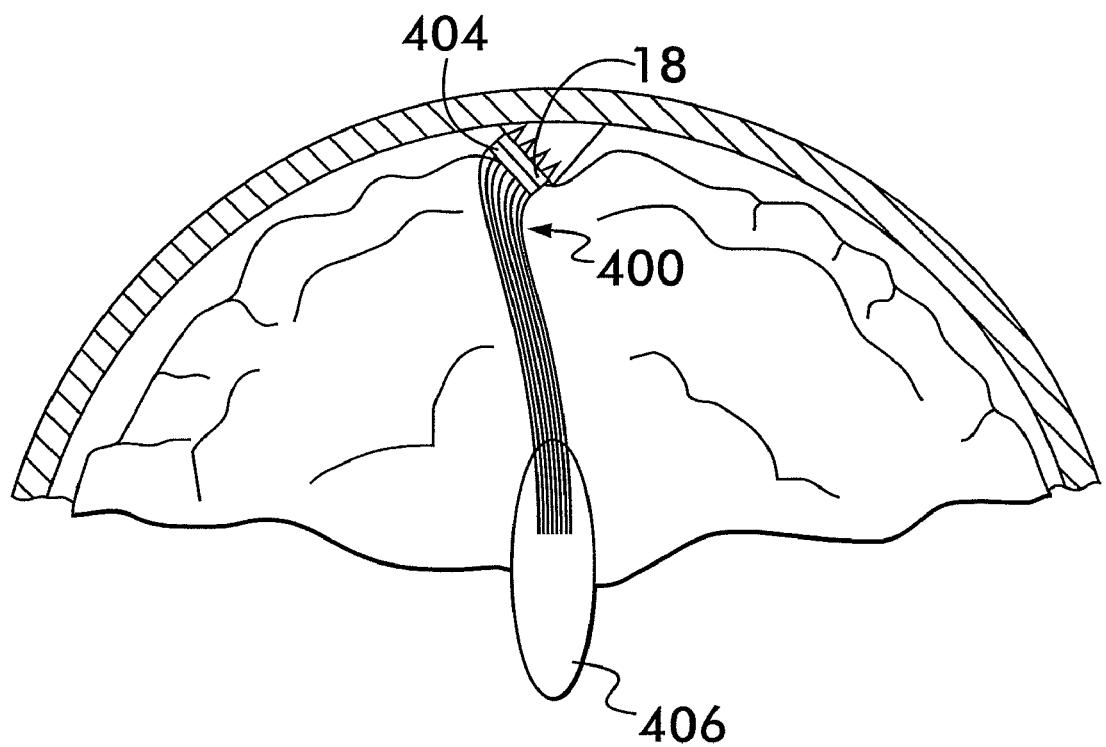
FIG. 9 is a schematic view of a portion of the second alternative embodiment, as viewed from the front of the head.

Referring to FIGS. 8 and 9, a second alternative embodiment of this invention is shown at 400. This embodiment functions in a similar manner to the first alternative embodiment shown in FIGS. 6, 7 and 7A. Specifically, instead of having micro-conduits 304 formed in a unitary fluid transmitting member 302 as in the embodiment 300, the embodiment 400 includes a plurality of individual fluid transmitting members in the form of micro-conduits or wicking, micro-fibers 402. These individual micro-conduits or micro-fibers 402 preferably have a length of approximately 5 centimeters and have a distal end communicating with a plenum compartment 404 and a proximal end communicating with the ventricular space 406. As illustrated, the fluid transmitting members 402 are shown in communication with the third ventricle 406. However, it is within the scope of this invention to also, or alternatively communicate the fluid transmitting members 402 with the lateral ventricles. By way of example, and not a limitation on the broadest aspects of this invention, the individual micro conduits can have an inside diameter of approximately 100 microns.

As can be seen in FIGS. 8 and 9, the plenum compartment 404, in the preferred embodiment of this invention, is coterminous with the substrate 18 and therefore all of the fluid transmitting micro-conduits or micro-fibers 402 communicate with all of the microvalves included in the substrate 18. However, it is within the scope of this alternative embodiment 400 to form the plenum compartment 404 of a dimension that does not communicate with all of the microvalves on the substrate 18. However, in the preferred embodiments of this invention the plenum compartment 404 should communicate with at least 50% and most preferably over 50% of the microvalves on the substrate 18. The plenum compartment 404 can be secured to the bottom surface of substrate 18 by any suitable means, such as an adhesive component that is biocompatible with the patient's body. The particular manner of securing, or fastening the plenum compartment 404 to the substrate 18 does not constitute a limitation on the broadest aspects of this invention.

It also should be apparent that the fluid transmitting members 402, including the plenum chamber 404 need to be formed of biocompatible materials in the same manner as the other components of this invention. This issue of material selection has been discussed in detail earlier in this application and will not be repeated herein for purposes of brevity. Suffice it to state that individuals skilled in the art clearly will be able to select suitable materials for use in the embodiment of this invention illustrated in FIGS. 8 and 9, and the specific materials employed do not constitute a limitation on the broadest aspects of this invention.

Turning to the methods of this invention, one method of fabricating the array of microneedles 12 on the substrate 14 is disclosed in an article entitled "Three dimensional MEMS microfluidic perfusion system for thick brain slice cultures," authored by Yoonsu Choi et al. and appearing in Biomed Microdevices (2007) 9:7-13. The subject matter of this latter article already has been fully incorporated by reference herein. In addition, the manner of forming the array of microneedles employed in the system 10 of this invention will be explained in connection with FIGS. 4A through 4E.

Figure 4A:
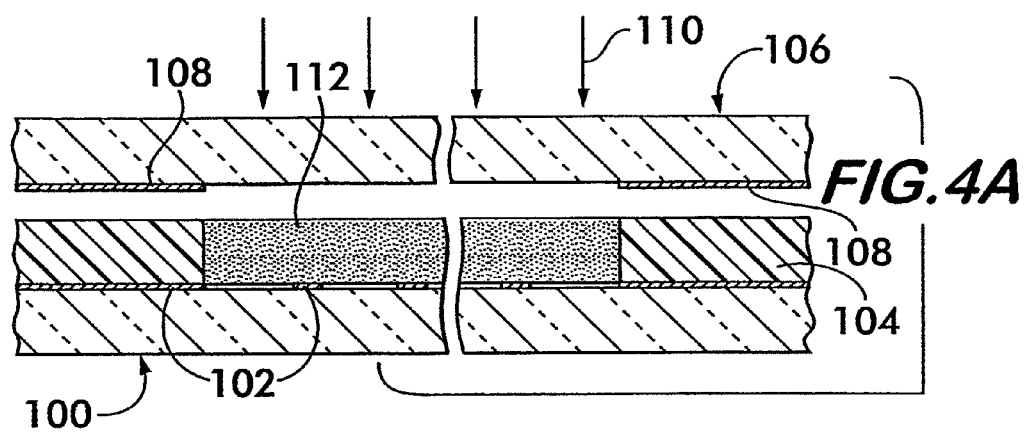

Referring to FIG. 4A, a glass substrate 100 is provided with a chromium coating 102 in a desired discontinuous pattern by a well-known photolithography-chrome etching process. In this well-known embodiment the discontinuous chrome pattern includes a chrome coating about the perimeter of the glass and a discontinuous pattern in the center that is spaced apart to provide uncoated regions in which the microneedles will be formed, as will be described in greater detail below.

A negative photoresist layer 104 is applied on the surface of the glass substrate 100 that includes the chrome etched pattern. This negative photoresist layer 104 crosslinks and hardens upon being exposed to ultraviolet (UV) radiation.

A second glass substrate 106 is provided with a chromium coating 108 about the periphery thereof by the same well-known photolithography-chrome etching process employed to form the chromium coating 102 on the glass substrate 100. The chrome coated, glass substrate 106 is placed over the photoresist layer 104 and UV light is directed through the substrate 106 in the direction illustrated by arrows 110. The UV radiation causes cross linking of the negative photoresist layer 104 to thereby harden the entire central region 112 of the layer 104 exposed to such radiation, as illustrated by the stippled section in FIG. 4A.

Figure 4B:
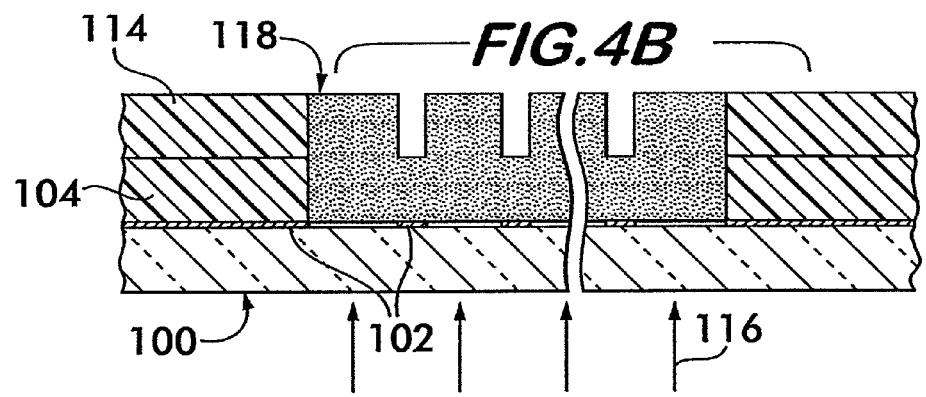
Figure 4C:
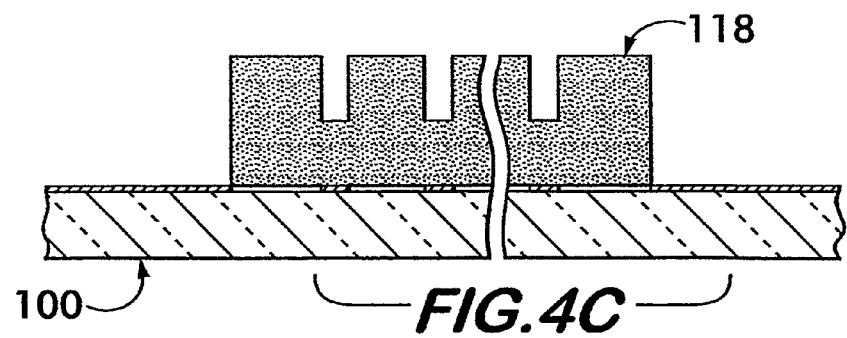

Referring to FIG. 4B, a second negative photoresist layer 114, which is the same as the photoresist layer 104, is then placed over the exposed, photoresist layer 104 and exposed to UV radiation directed through the glass substrate 100 in the direction illustrated by arrows 116. Only regions of the photoresist layer 114 aligned with the spaces between the discontinuous chrome pattern on glass substrate 100 will be exposed to, and hardened by the UV radiation indicated by arrows 116. These hardened regions of the layer 114 are illustrated by the stippled section forming a unitary structure 118 with the hardened section 112 of the layer 104. Referring to FIG. 4C, the unexposed regions of the photoresist layers 104, 114 are then dissolved away, leaving only the unitary structure 118.

Thereafter, the peaks of the unitary structure 118, formed from the photoresist layer 114, are sharpened by oxygen plasma etching into cone-shaped members to form the structure 120 shown in FIG. 4D. In addition, the chrome-coated glass substrate 100 is removed.

Thereafter, the structure 120 is subject to laser machining from both sides thereof to form the final configuration of the array of microneedles 12 on the substrate 14, as illustrated by the structure 122 in FIG. 4E.

To complete the formation of the microneedles 12 and substrate 14 employed in the system 10, the structure 122 is provided with a biocompatible coating of polyparaxylylene in a conventional manner (not shown).

The manner of making the array of dome petal valves 16 employed in the preferred embodiment of this invention will now be described in connection with FIGS. 5A-5H. In addition, a Parylene check valve system useable in this invention also is disclosed in an article titled: "A Parylene Micro Check Valve," authored by Xuan-Oi Wang, et al., and appearing in the Proceedings of the IEEE Micro Electro Mechanical Systems (MEMS, 1999, pgs. 177-182 beginning on page 177 of the IEEE publication in 1999.

First, a glass substrate 200 is provided with a layer 202 of polyparaxylylene (Parylene C), as shown in FIG. 5A. Thereafter, a conventional photolithography/ion etching process is employed to form opening 203 in the layer 200, as shown in FIG. 5B.

Thereafter, a thick, positive photoresist material 204 is applied on the polyparaxylylene layer 202 in a region centered over the hole 203, as shown in FIG. 5C. A positive photoresist material softens when exposed to heat. The photoresist material 204 is heated to cause it to reflow into a generally dome-shaped configuration, as shown in FIG. 5D. Thereafter a polyparaxylylene layer 206 is applied over the dome shaped material 204 and over the portion of the layer 200 of polyparaxylylene surrounding said dome shaped material, as also is illustrated in FIG. 5D.

Referring to FIG. 5E, upstanding walls 208 are then formed, which provides the perimeter of the valve structure, as also is shown in FIGS. 2 and 3. These walls 208 are formed from the same negative photoresist material employed to form the microneedles 12, and are formed by the same masking/UV exposure technique discussed above in connection with the fabrication of the microneedles 12.

Thereafter, a laser machining operation is employed to form the four valve petals 210 in the dome shaped photoresist material 204, as illustrated in FIGS. 5F and 5G. It should be noted that for purpose of clearly illustrating the four-petal construction of the valve 16 the walls 208 of the valve are omitted from FIG. 5H.

In a representative embodiment the dome shaped membrane formed into the four petals 210 has a thickness of approximately 1-5 micrometers and the substrate 18 has a thickness of approximately 20 micrometers.

Although illustrated and described herein with reference to certain specific embodiments, the present invention is nevertheless not intended to be limited to the details as shown. Rather, various modifications may be made in the details within the scope and range of equivalence of the claims and without departing from the spirit of the invention.

What is claimed is:

1. An implantable system for the treatment of hydrocephalus, said system including:
   (a) a plurality of hollow microneedles in a fixed array relative to each other, said microneedles having passages therethrough and being of a size to extend through dura mater with a proximal end on one side of the dura mater and a distal end communicating with the venous system in an area on a second side of the dura mater opposed to said one side;
   (b) an array of microvalves associated with a proximal end of said microneedles, said microvalves including segments movable by a pressure build up of cerebrospinal fluid (CSF) within the interior of the brain to provide open communication between the interior of the brain on said one side of the dura mater and the venous system on the second side of the dura mater through the passages in the microneedles for permitting the flow of CSF through the dura mater from the proximal end to the distal end of each microneedle;
   (c) a plurality of fluid transmitting members having distal ends communicating with the microvalves in said array of microvalves and proximal ends communicating with the ventricular space of the brain, said fluid transmitting members being micro-conduits or micro-fibers configures to transmit from the ventricular space through the microvalves and micro needles in fluid communication with said fluid transmitting members to prevent an excessive pressure build up of CSF within the interior of the brain.

2. The system of claim 1, wherein said microvalves permit the flow of CSF through the microneedles based on the pressure differential between the ventricular space at the proximal end of the fluid transmitting members and the sinus at the distal end of said needles.

3. The system of claim 1, wherein said fluid transmitting members have distal ends communicating with more than 50% of the microvalves in said array of microvalves.

4. The system of claim 1, wherein said fluid transmitting members have distal ends communicating with all of the microvalves in said array of microvalves.

5. The system of claim 1, wherein said fluid transmitting members include hollow micro-conduits.

6. The system of claim 1, wherein said fluid transmitting members include wicking, micro-fibers.

7. The system of claim 1, wherein said plurality of fluid transmitting members communicate with a plenum chamber at a distal end of said fluid transmitting members, said plenum chamber being secured in overlying relationship and in communication with said microvalves.

8. The system of claim 1, wherein said plurality of fluid transmitting members communicate with a plenum chamber at a distal end of said fluid transmitting members, said plenum chamber being secured in overlying relationship and in communication with more than 50% of said microvalves.

9. The system of claim 1, wherein said plurality of fluid transmitting members communicate with a plenum chamber at a distal end of said fluid transmitting members, said plenum chamber being secured in overlying relationship and in communication with all of said microvalves.

10. The system of claim 7, wherein said plurality of fluid transmitting members and plenum chamber are a unitary member.

11. The system of claim 8, wherein said plurality of fluid transmitting members and plenum chamber are a unitary member.

12. The system of claim 9, wherein said plurality of fluid transmitting members and plenum chamber are a unitary member.

13. The system of claim 1, wherein the proximal ends of said fluid transmitting members are within the third ventricle.

14. The system of claim 1, wherein the proximal ends of said fluid transmitting members are within one or more lateral ventricles.

15. The system of claim 1, wherein said plurality of microneedles are formed in a fixed array on a first substrate and the microvalves are formed in fixed array on a second substrate, said first and second substrates being contiguous to each other to thereby communicate each microvalve on the second substrate with the proximal end of a corresponding microneedle.

16. The system of claim 15, wherein said microvalves each include an upstanding peripheral wall positioned within an opening in the first substrate that communicates with a proximal end of a corresponding microneedle.

17. The system of claim 16, wherein an outer surface of the peripheral walls of each microvalve frictionally engage internal surfaces defining the opening in the first substrate.

18. The system of claim 1, wherein said first and second substrates are secured together.

19. The system of claim 1, wherein said microneedles are biocompatible with the human body.

20. The system of claim 1, wherein at least some of the microneedles are generally cone-shaped and have a recess in an outer surface thereof for receiving dura mater therein to help retain the system in proper position when implanted.

* * * * *